United States Patent [19]

Steiner et al.

[11] Patent Number: 4,866,057
[45] Date of Patent: Sep. 12, 1989

[54] 4-SUBSTITUTED 10-CYANOMETHYLENEPYRROLO[4,3-E]-BENZAZEPINES

[75] Inventors: Gerd Steiner, Kirchheim; Juergen Pfister, Frankenthal; Hans-Juergen Teschendorf, Dudenhofen; Liliane Unger, Ludwigshafen; Rudolf Binder, Worms, all of Fed. Rep. of Germany

[73] Assignee: BASF Aktiengesellschaft, Ludwigshafen, Fed. Rep. of Germany

[21] Appl. No.: 196,606

[22] Filed: May 20, 1988

[30] Foreign Application Priority Data

May 21, 1987 [DE] Fed. Rep. of Germany ....... 3717068

[51] Int. Cl.⁴ .................. C07D 487/04; A61K 31/55
[52] U.S. Cl. ..................................... 514/215; 540/577
[58] Field of Search ......................... 540/577; 514/215

[56] References Cited

U.S. PATENT DOCUMENTS

| 4,362,727 | 12/1982 | Steiner et al. | 514/215 |
| 4,388,237 | 6/1983 | Steiner et al. | 514/215 |
| 4,745,111 | 5/1988 | Steiner | 514/215 |

FOREIGN PATENT DOCUMENTS

| 3037971 | 5/1980 | Fed. Rep. of Germany | 514/215 |
| 2918778 | 11/1980 | Fed. Rep. of Germany | 514/215 |
| 3524744 | 1/1987 | Fed. Rep. of Germany | 514/215 |

OTHER PUBLICATIONS

J. Schmutz, "Neuroleptic Piperazinyl–dibenzo–azepines," *Arzneim. Forsch.*, 25, pp. 712–720 (1975).

Primary Examiner—Robert Gerstl
Attorney, Agent, or Firm—Oblon, Spivak, McClelland, Maier & Neustadt

[57] ABSTRACT

Compounds of the formula

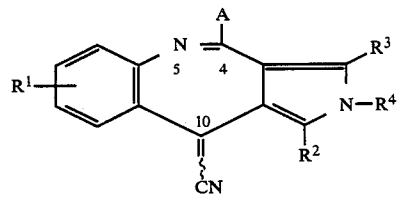

where $R^1$, $R^2$, $R^3$, $R^4$ and A have the meanings stated in the specification, as well as the use thereof for controlling diseases, are described.

11 Claims, No Drawings

4-SUBSTITUTED 10-CYANOMETHYLENEPYRROLO[4,3-E]-BENZAZEPINES

The present invention relates to 10-cyanomethylenepyrrolo-[4,3-e]benzazepines substituted in the 4-position, to a process for the preparation thereof, and to the use thereof as drugs which can be employed as sedatives, hypnotics, tranquilizers, muscle relaxants, neuroleptics or antiparkinson agents.

It is known that tricyclic ring systems with a dibenzo structure to a central heterocyclic 7-ring, which optionally has an N-methylpiperazino radical, have neuroleptic effects. Examples of such tricyclics are N-methylpiperazine derivatives of dibenzo[b,e][1,4]diazepines (clozapine), dibenzo[b,f][1,4]thiazepines (clotiapine), dibenzo[b,f][1,4]oxazepines (loxapine) or morphanthridines (perlapine), as are disclosed, for example, in the compilation of J. Schmutz in Arzheim-Forsch. 25 (1975) 712–720.

German Laid-Open Applications Nos. DOS 2,918,778, DOS 3,037,971 and DOS 3,524,744 describe 6-substituted 11-alkylenemorphanthridines, 5-substituted 9-cyanomethylenedithieno[3,4-b:4′,3′-e]azepines and 4-substituted 10-cyanomethylenethieno[4,3-e]benzazepines with valuable pharmacological properties.

We have now found that 4-substituted 10-cyanomethylenepyrrolo[4,3-e]benzazepines of the formula I

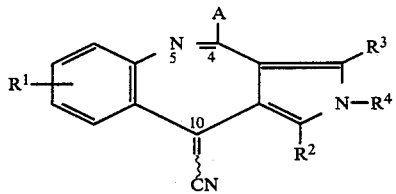

(I)

where $R^1$ is hydrogen or halogen, alkyl of 1 to 3 carbon atoms, trifluoromethyl or alkoxy of 1 to 3 carbon atoms, $R^2$ and $R^3$ are hydrogens or halogens, $R^4$ is hydrogen or alkyl of 1 to 3 carbon atoms or aralkyl where alkyl is of 1 to 3 carbon atoms and where the aromatic system may be substituted by halogen, $C_{1-3}$alkyl or methoxy, and A is an amino radical $-NR^5R^6$ where $R^5$ and $R^6$ form, together with the nitrogen atom connecting them, a 5- to 7-membered saturated ring which may contain a nitrogen or oxygen as further hetero atom, it being possible for an additional nitrogen to be substituted by alkyl of 1 to 3 carbon atoms, hydroxyalkyl of 2 to 3 carbon atoms, alkoxyalkyl where alkyl or alkoxy is of 2 or 3 carbon atoms, cycloalkyl or cycloalkylmethyl with 3 to 7 carbon atoms in the cycloalkyl ring, alkynyl of 2 to 5 carbon atoms and additionally by oxygen in the form of an N-oxide, or A is an amino radical $-NHR^7$ where $R^7$ is aminoalkyl of 2 to 7 carbon atoms, it being possible for the amine nitrogen to be substituted by alkyl of 1 to 5 carbon atoms or to be a constituent of a 5- to 7-membered saturated ring which may contain a nitrogen or oxygen as further hetero atom, it being possible for a nitrogen which is present to be substituted by alkyl of 1 to 3 carbon atoms or hydroxyalkyl of 2 or 3 carbon atoms, and the physiologically tolerated acid addition salts thereof have valuable pharmacological properties.

Particularly suitable meanings for $R^1$ are the following: hydrogen, fluorine, chlorine, methyl, trifluoromethyl and methoxy.

An $-NR^5R^6$ amino radical A is preferably piperazinyl, homopiperazinyl, piperidinyl or morpholinyl.

Particularly preferred for $-NR^5R^6$ are 4-methylpiperazinyl, the 4-oxide of 4-methylpiperazinyl, 4-ethylpiperazinyl and N-methylhomopiperazinyl.

In the amino radical $-NHR^7$, $R^7$ is preferably 2-dimethylaminoethyl or 2-piperidin-1-ylethyl.

It is to be noted that the novel compounds of the formula I exist as (E) and (Z) isomers Ia and b.

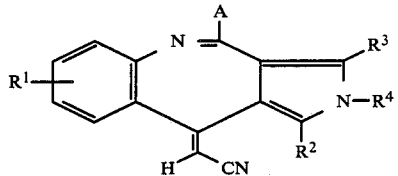

Ia

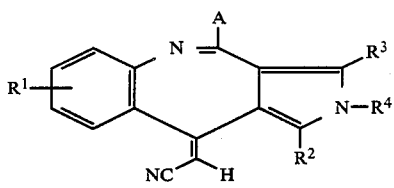

Ib

The (E) and (Z) isomers can be separated, for example, by fractional crystallization or by column chromatography. The assignment of the individual isomers is carried out, for example, by X-ray structure analysis, as is evident from the Examples.

The following compounds are particularly preferred:
(E),(Z)-10-cyanomethylene-4-(4-methyl-1-piperazinyl)-pyrrolo[4,3-e]benzazepine
(Z)-10-cyanomethylene-4-(4-methyl-1-piperazinyl)pyrrolo[4,3-e]benzazepine
(E)-10-cyanomethylene-4-(4-methyl-1-piperazinyl)pyrrolo[4,3-e]benzazepine
(E),(Z)-7-chloro-10-cyanomethylene-4-(4-methyl-1-piperazinyl)pyrrolo[4,3-e]benzazepine.

The novel compounds of the formula I are prepared by reacting a compound of the formula II

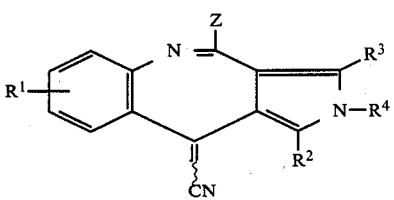

(II)

where $R^1$, $R^2$, $R^3$ and $R^4$ have the stated meanings, and Z is a nucleofugic leaving group, with a nucleophile AH in which A has the meanings stated for formula I, where appropriate separating into the pure (E) and (Z) isomers and/or where appropriate converting the resulting compound into the N-oxide and/or into the acid addition salt of a physiologically tolerated acid.

Suitable and preferred nucleofugic leaving groups for Z are halogens, in particular bromine or chlorine.

The reaction is expediently carried out in the presence of an excess of the amine AH used, which simultaneously acts as solvent and, where appropriate, as acid-binding agent. It is possible, where appropriate, to operate in the presence of an inert solvent such as a cyclic saturated ether, especially tetrahydrofuran or dioxane, of benzene or of an aromatic hydrocarbon such as toluene, xylene, mesitylene or decahydronaphthalene, or of an aprotic polar solvent such as dimethylformamide. If only one equivalent of the amine AH is used, it is necessary also to add one equivalent of an inert base such as, for example, triethylamine.

The reaction is usually carried out at 80° to 150° C. and is generally complete within 1 to 10 hours. It may be advantageous to exclude atmospheric oxygen and to work under an inert gas, for example under nitrogen. The nucleophile AH is advantageously used in the reactions in a not less than 2- and up to 20-fold molar excess.

The conversion of a compound of the formula I into the N-oxide is carried out in a conventional manner, expediently using aqueous hydrogen peroxide (30% strength by weight) in ethanolic solution or using a peroxy acid in a halohydrocarbon. The conversion into the acid addition-salt salt of a physiologically tolerated acid is likewise carried out in a conventional manner.

The starting compounds of the formula II are obtained by refluxing a 10-cyanomethylene-4,5-dihydropyrrolo[4,3-e]benzazepin-4-one of the formula III

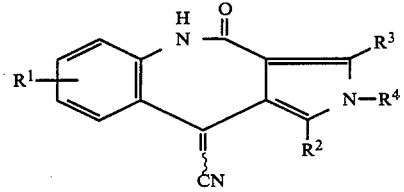

where $R^1$, $R^2$, $R^3$ and $R^4$ have the meanings stated for formula II, with an excess of halogenating agent, such as phosphorus oxychloride, in the presence of a solvent, preferably in a halohydrocarbon, and in the presence of a catalytic amount of N,N-dimethylaniline for from 1 to 5 hours, and isolating the resulting imino chloride after the excess phosphorus oxychloride has been removed by distillation and working up in an aqueous two-phase system by extraction with a chlorinated hydrocarbon such as methylene chloride.

The novel 10-cyanomethylene-4,5-dihydropyrrolo[4,3-e]benzazepin-4-one of the formula III, in which $R^1$, $R^2$, $R^3$ and $R^4$ have the meanings stated for the formula I, is prepared by forming an olefin from the carbonyl by reacting a 4,5-dihydropyrrolo[4,3-e]benzazepine-4,10-dione of the formula IV

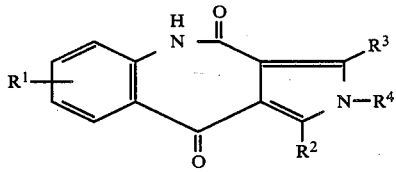

with a phosphonate of the formula Va

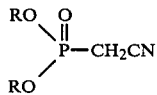

where R is alkyl of 1 to 3 carbon atoms, under the conditions of the Wittig-Horner reaction in dimethylformamide and in the presence of one mole-equivalent of sodium t-butylate, at from 20° to 100° C., or with a phosphonium salt of the formula Vb

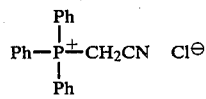

where Ph is phenyl, under the conditions of the classical Wittig reaction in dimethylformamide in the presence of one mole-equivalent of sodium ethylate, at from 20° to 100° C.

The novel 4,5-dihydropyrrolo[4,3-e]benzazepine-4,10-dione of the formula IV, in which $R^1$, $R^2$, $R^3$ and $R^4$ have the meanings stated for formula I, is prepared by Friedel-Crafts cyclization by cyclizing a phenylamide of a pyrrole-3,4-dicarboxylic acid, of the formula VI

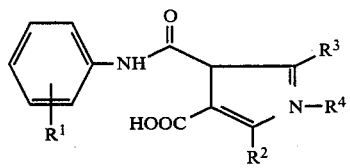

in the presence of a strong acid, preferably in polyphosphoric acid, which also acts as solvent, at from 20° to 150° C., for 1 to 3 hours.

The phenylamide of the pyrrole-3,4-dicarboxylic acid, of the formula VI, is obtained in a simple manner by reacting the pyrrole-3,4-dicarboxylic anhydride with the appropriate aniline in an inert organic solvent such as, for example, methylene chloride, at room temperature for 1 to 5 hours.

The pyrrole-3,4-dicarboxylic anhydrides are produced from the pyrrole-3,4-dicarboxylic acids which have the substituent $R^4$ on the nitrogen and are known from the literature (Bull. Soc. Chim. Fr. 1975, 2335; J. Heterocycl. Chem. 1983, 20(2), 321) by heating with acetic anhydride at from 20° to 150° C. in a conventional manner.

The novel compounds of the formula I are usually obtained in the form of yellowish or yellow crystals and can be purified by recrystallization from the customary organic solvents, preferably from a lower alcohol, such as ethanol, or by column chromatography.

If necessary, the individual (E) and (Z) isomers are separated by fractional crystallization in a chlorinated hydrocarbon, preferably methylene chloride, a lower monohydric alcohol, preferably methanol or ethanol, or a saturated cycloaliphatic hydrocarbon, preferably cyclohexane, or by column chromatography over silica gel, in particular with methylene chloride and methanol in the ratio of from 99:1 to 85:15 parts by volume.

The free substituted 10-cyanomethylenepyrrolo[4,3-e]benzazepines of the formula I can be converted in a conventional manner into the acid addition salt of a pharmacologically tolerated acid, preferably by adding one equivalent of the appropriate acid to a solution. Examples of pharmaceutically tolerated acids are hydrochloric acid, phosphoric acid, sulfuric acid, methanesulfonic acid, sulfamic acid, maleic acid, fumaric acid, oxalic acid, tartaric acid and citric acid.

The novel compounds have valuable pharmacological properties. They can be used as sedatives, hypnotics, tranquilizers, muscle relaxants, neuroleptics or antiparkinson agents. It is possible for one novel compound to combine several of the said types of action. In some cases, the single pure isomer obtained after separation of the isomers may preferentially exhibit an action. Hence the novel substances are suitable for the treatment of psychological disturbances, in particular schizophrenia, anxiety, excited state and disturbances of the extrapyramidal motor system, for example Parkinson's disease.

The following methods have been employed to characterize the actions:

1. Sedative action 4 to 8 groups each comprising 3 female NMRI mice receive the substances by oral administration. The orientation hypermotility induced by a new environment is determined photoelectrically 30 min after the administration of the substance for a period of 30 min.

The $ED_{50}$ is determined as the dose which brings about a decrease in the orientation hypermotility of 50% compared with placebo-treated control animals.

2. L-5-HTP antagonism (serotonin antagonism)

L-5-Hydroxytryptamine (L-5-HTP), a serotonin prodrug, causes in rats (316 mg/kg i.p.) a state of agitation which is characterized by signs such as head-shaking, tremor and movements of the forepaws. The animals are observed for 1 h after administration of L-5-HTP, and the signs are scored every 10 min. The test substances are administered orally 1 h before L-5-HTP; n/dose=6. The $ED_{50}$ is calculated as the dose which brings about a mean reduction in the score of a control group by 50%.

3. Anticholinergic action

Groups of 10 female NMRI mice receive physostigmine in a lethal dose (0.825 mg/kg) subcutaneously. The test substances are administered orally 30 min before the physostigmine administration. The $ED_{50}$ is determined as the dose of substance which protects 50% of the animals from death due to physostigmine.

4. In vitro determination of the affinity to dopamine $D_1$ and $D_2$ receptors by means of competitive assays Based on the method of Seeman et al. (J. Neurochem. 43 (1984) 221-235), 1 ml mixtures containing bovine nucleus caudatus membranes in 50 mM Tris-HCl buffer, pH 7.4, with 120 ml NaCl, 5 mM KCl, 1 mM $MgCl_2\times 6$ $H^2O$ and 2 mM $CaCl_2\times 2$ $H_2O$ and with increasing concentrations of test substance and a fixed concentration of the dopamine $D_1$ or $D_2$ receptor ligand $^3$H-SCH 23390 (1 nM) or $^3$H-spiperon (0.2 nM) were prepared. The non-specific binding was determined using 10 μM (+)-butaclamol or using 1 μM haloperidol. After incubation at 30° C. for 60 min, the mixtures were filtered through glass fiber filters (GF/B, Whatman) and the amount of radioligand retained on the filter was determined by liquid scintillation measurement.

The competition constants ($K_i$ values) were calculated by non-linear regression analysis on an IBM computer based on the "Ligand" program of Munson and Rodbard (Anal. Biochem. 107 (1980) 220).

TABLE 1

| Substance of Example | Sedative action mouse ED 50 mg/kg oral | Antiserotoninergic action rat ED mg/kg oral | Anticholinergic mouse ED 50 mg/kg oral |
|---|---|---|---|
| 1a | 2.96 | 1.18 | >21.5 |
| 3 | 0.82 | 0.2 | 17.5 |

TABLE 1-continued

| Substance of Example | Sedative action mouse ED 50 mg/kg oral | Antiserotoninergic action rat ED mg/kg oral | Anticholinergic mouse ED 50 mg/kg oral |
|---|---|---|---|
| 3a | 0.67 | 0.29 | |
| 9 | 29.8 | 46.4 | >46.4 |
| 11 | 35.0 | | >100 |
| 12 | 4.7 | 3.3 | 16.7 |
| Clozapine | 3.8 | 6.3 | 14.1 |

TABLE 2

| Substance of Example | Affinity to $D_1$ receptor Inhibition of $^3$H—SCH 23 390 binding Ki (nM) | Affinity to $D_2$ receptor Inhibition of $^3$H—spiperon binding Ki (nM) |
|---|---|---|
| 1a | 10.5 | about 2000 |
| 3 | 20.0 | about 1000 |
| 9 | 3.4 | about 1000 |
| 11 | 12.8 | about 1000 |
| 12 | 20.8 | about 2000 |
| Clozapine | 172 | 270 |

In the investigations carried out, in which sedatives and minor and major tranquilizers show typical actions, the novel compounds are found to have satisfactory actions with the action of the reference substance clozapine usually being reached or exceeded. This applies to Examples 1a and 3 for the sedative action and to Examples 1a, 3 and 12 for the antiserotoninergic action.

A difference by comparison with clozapine, and thus a new action profile, emerges in the antidopaminergic action which was measured biochemically as affinity to the $D_1$ receptor and to the $D_2$ receptor. Whereas with clozapine the affinity to the $D_1$ receptor is slightly higher than that of the $D_2$ receptor, the novel substances are selective $D_1$ antagonists. The Ki values for displacement from the $D_1$ receptor are about 50 to 300 times lower than the Ki values for displacement from the $D_2$ receptor. Furthermore, the strength of the $D_1$ antagonistic action of clozapine is distinctly exceeded by the new substances (a factor of 8 to 50).

The anticholinergic action is less pronounced, which is an advantage in view of the clinical side effects brought about by this.

Accordingly, the invention also relates to a therapeutic agent containing a compound of the formula I or a pharmacologically tolerated acid addition salt thereof as active compound in addition to customary vehicles and diluents, as well as to the use of the novel compounds for controlling diseases.

The novel compounds can be administered in a conventional manner orally or parenterally, intravenously or intramuscularly.

The dosage depends on the age, condition and weight of the patient and on the mode of administration. As a rule, the daily dose of active compound is from about 1 to about 20 mg/kg of body weight on oral administration and from 0.1 to 2 mg/kg of body weight on parenteral administration.

The novel compounds can be used in conventional solid or liquid pharmaceutical administration forms, for example as tablets, film-coated tablets, capsules, powders, granules, sugar-coated tablets, suppositories, solutions, ointments, creams or sprays. These are prepared in a conventional manner. It is possible in this connection for the active compounds to be processed with the customary pharmaceutical auxiliaries such as tablet binders, fillers, preservatives, tablet disintegrants, flow regulators, emollients, wetting agents, dispersing agents, emulsifiers, solvents, retardants, antioxidants and/or propellant gases (cf. H. Sucker et al.: Pharmazeutische Technologie (Pharmaceutical technology) published by Thieme, Stuttgart, 1978). The administration forms obtained in this way normally contain 0.1 to 99% by weight of the active compound.

The Examples which follow serve to illustrate the invention:

EXAMPLE 1

A Preparation of the starting materials (a) N-Methylpyrrole-3,4-dicarboxylic anhydride 30.4 g (180 mmol) of N-methylpyrrole-3,4-dicarboxylic acid were refluxed with 250 ml of acetic anhydride for 1 h. Subsequently a total of about 200 ml of acetic anhydride mixed with acetic acid was removed by distillation through a column head for 4 h. Filtration was followed by the mixture being evaporated to dryness, 50 ml of toluene being added and evaporation to dryness being repeated. After another repetition of this operation, 37.6 g of product were isolated as crystal/oil mixture which still contained some acetic anhydride but was sufficiently pure for further reaction.

(b) Monophenylamide of N-methylpyrrole-3,4-dicarboxylic acid 16.0 g (172 mmol) of aniline in 20 ml of methylene chloride were added dropwise to 20.0 g (132 mmol) of N-methylpyrrole-3,4-dicarboxylic anhydride in 80 ml of methylene chloride while stirring vigorously at room temperature. The mixture was subsequently left to stir for 5 h, and then the thick precipitate of solid was filtered off with suction and thoroughly washed with methylene chloride, and the solid was dried first in air and later under reduced pressure. The yield was 19.8 g (61%), melting point 248°–250° C.

(c) 2-Methyl-4,5-dihydropyrrolo[4,3-e]benzazepine-4,10-dione 19.2 g (79 mmol) of the monophenylamide of N-methylpyrrole-3,4-dicarboxylic acid were introduced a little at a time into 240 g of polyphosphoric acid while stirring vigorouly at an internal temperature of 100° C., and the mixture was then stirred at an internal temperature of 115°–120° C. for 1 h. After cooling the mixture was poured onto ice/water, leaving to stir for 1 h. After the mixture had stood overnight, the fine pale brown crude product was filtered off with suction, thoroughly washed with water and dried in a vacuum drying oven at 60° C. 13.4 g (75%) of product, melting point >280° C., which is sufficiently pure for further reaction, were isolated.

(d) (E),(Z)-10-Cyanomethylene-2-methyl-4,5-dihydropyrrolo[4,3-e]benzazepin-4-one (mixture of (E) and (Z) isomers)

To prepare this product, an olefin was formed from a carbonyl of 2-methyl-4,5-dihydropyrrolo[4,3-e]benzazepine-4,10-dione by means of the Wittig-Horner reaction ($\alpha$) or by classical Wittig synthesis ($\beta$):

($\alpha$) 9.6 g (43 mmol) of 2-methyl-4,5-dihydropyrrolo[4,3-e]benzazepine-4,10-dione were dissolved in 70 ml of dimethylformamide, heating at 60°–70° C., and stirred under nitrogen. Then 15.0 g (85 mmol) of diethyl cyanomethylphosphonate were then added dropwise, and 9.5 g (85 mmol) of potassium tertiary-butylate were added a little at a time at an internal temperature of 60°–70° C. while stirring vigorously. The mixture was then left to stir at 80° C. for 2 h.

After removal of the solvent under reduced pressure, the residue was taken up in 400 ml of ice/water, and the mixture was acidified with a little 10% strength hydrochloric acid, left to stir while cooling for 1 h, and the pale brown crude product was filtered off with suction, washing copiously with water. After drying in vacuo at 60° C., 10.2 g (95%) of product, melting point 277°–280° C., were obtained.

($\beta$) Triphenylcyanomethylphosphonium chloride was introduced into dimethylformamide, and then 1 mole-equivalent of a 30% strength sodium methylate solution was added dropwise, or 1 mole-equivalent of sodium hydride was added, and finally 1 mole-equivalent of a solution of 2-methyl-4,5-dihydropyrrolo[4,3-e]benzazepine-4,10-dione in di-methylformamide was added. The reaction mixture was then left to stir at 50° to 80° C. for 5 to 8 h and subsequently poured onto ice/water, and the mixture was extracted several times with methylene chloride. Drying and concentration of the organic phase yielded the crude product. Yield: 67% of colorless crystals, melting point 275°–279° C.

B Preparation of the final product (E)- and (Z)-10-Cyanomethylene-2-methyl-4-(4-methyl-1-piperazinyl)pyrrolo[4,3-e]benzazepine (a) 20 ml of phosphorus oxychloride and 0.2 ml of N,N-dimethylaniline were added to 5.8 g (23 mmol) of 10-cyanomethylene-2-methyl-4,5-dihydropyrrolo[4,3-e]benzazepin-4-one (mixture of (E) and (Z) isomers) in 70 ml of 1,1,1-trichloroethane, and the mixture was refluxed under a nitrogen atmosphere for 1 h. After the excess phosphorus oxychloride and dimethylaniline had been completely removed by distillation under oil pump vacuum, the residue was partitioned between methylene chloride and water, the mixture was filtered, the aqueous phase was extracted twice more with methylene chloride, and the combined or—ganic phases were washed thoroughly with dilute hydrochloric acid and water. Drying and concentration of the organic phase provided 5.8 g (95%) of 4-chloro-10-cyanomethylene-2-methylpyrrolo[4,3-e]benzazepine which is sufficiently pure for further reaction.

5.8 g (22 mmol) of 4-chloro-10-cyanomethylene-2-methylpyrrolo[4,3-e]benzazepine were dissolved in 50 ml of dimethylformamide, 6.6 ml (60 mmol) of N-methylpiperazine were added (strongly exothermic reaction) and the mixture was stirred at 80° C. under nitrogen for 1 h. After removal of the solvent under reduced pressure the residue was taken up in about 200 ml of ice/water, the mixture was make alkaline with a little 10% strength sodium hydroxide solution and then stirred while cooling for 1 h and the pale brown crude product was filtered off with suction, washing copiously with water. The crude product was purified by column chromatography (silica gel, mobile phase 95/5 methylene chloride/methanol). 5.3 g (73%) of yellowish 10-cyanomethylene-2-methyl-4-(4-methyl-1-piperazinyl)pyrrolo-[4,3-e]benzazepine were obtained in the form of a mixture of the (E) and (Z) isomers, which was recrystallized from isopropanol: melting point 178°–180° C.

(b) To separate the (E) and (Z) isomers, the mixture of isomers was enriched by column chromatography (silica gel, mobile phase 95/5 methylene chloride/methanol) in the non-polar and polar fraction, and each of the two enriched geometric isomers were subjected to fractional recrystallization from isopropanol. This resulted in virtually pure (E) and (Z) isomers.

The (E) isomer a was isolated as the non-polar component (thin-layer chromatography, silica gel, mobile phase 85/15 toluene/methanol) in a yield of 1.8 g and with melting point 208°–210° C.

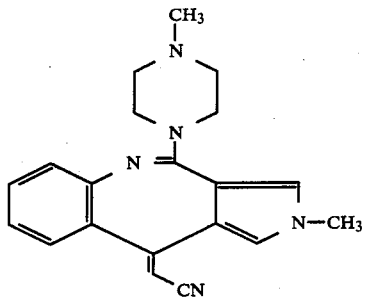

EXAMPLE 2

(E),(Z)-10-Cyanomethylene-2-methyl-4-(4-methyl-1-piperazinyl 4-oxide)pyrrolo[4,3-e]benzazepine×2.5 H₂O 2.0 g (6.0 mmol) of cis,trans-10-cyanomethylene-2-methyl-4-(4-methyl-1-piperazinyl)pyrrolo[4,3-e]benzazepine (cf. Example 1) were dissolved in 100 ml of methylene chloride, and 1.3 g (6.0 mmol) of 3-chloroperoxybenzoic acid were added. The mixture was then stirred at room temperature for one hour and subsequently diluted with 100 ml of methylene chloride, and about 100 ml of H₂O were added, and the pH was adjusted to 12 with 10% strength sodium hydroxide solution. The aqueous phase was extracted several more times with methylene chloride, and the combined organic phases were dried and concentrated, and the resulting N-oxide was purified by column chromatography (silica gel, mobile phase 1/1 methylene chloride/methanol). 1.2 g (58%) of yellow crystals were isolated, melting point 158°–160° C.

The following substances are obtained in analogy to Examples 1 and 2 using the appropriate substituted starting compounds:

3. (E),(Z)-7-Chloro-10-cyanomethylene-2-methyl-4-(4-methyl-1-piperazinyl)pyrrolo[4,3-e]benzazepine.
3a. (E)-7-Chloro-10-cyanomethylene-2-methyl-4-(4-methyl-1-piperazinyl)pyrrolo[4,3-e]benzazepine.
4. (E),(Z)-7-Fluoro-10-cyanomethylene-2-methyl-4-(4-methyl-1-piperazinyl)pyrrolo[4,3-e]benzazepine.
5. (E),(Z)-7-Methyl-10-cyanomethylene-2-methyl-4-(4-methyl-1-piperazinyl)pyrrolo[4,3-e]benzazepine.
6. (E),(Z)-7-Trifluoromethyl-10-cyanomethylene-2-methyl-4-(4-methyl-1-piperazinyl)pyrrolo[4,3-e]benzazepine.
7. (E),(Z)-7-Methoxy-10-cyanomethylene-2-methyl-4-(4-methyl-1-piperazinyl)pyrrolo[4,3-e]benzazepine.
8. (E),(Z)-10-Cyanomethylene-4-(4-methyl-1-piperazinyl)pyrrolo[4,3-e]benzazepine.
9. (E),(Z)-10-Cyanomethylene-2-benzyl-4-(4-methyl-1-piperazinyl)pyrrolo[4,3-e]benzazepine.
10. (E),(Z)-10-Cyanomethylene-1,3-dichloro-2-methyl-4-(4-methyl-1-piperazinyl)pyrrolo[4,3-e]benzazepine.
11. (E),(Z)-7-Chloro-2-benzyl-10-cyanomethylene-4-(4-methyl-1-piperazinyl)pyrrolo[4,3-e]benzazepine.
12. (E),(Z)-10-Cyanomethylene-2-methyl-4-(4-ethyl-1-piperazinyl)pyrrolo[4,3-e]benzazepine.
13. (E),(Z)-10-Cyanomethylene-2-methyl-4-(2-piperidin-1-yl)ethylaminopyrrolo[4,3-e]benzazepine.
14. (E),(Z)-10-Cyanomethylene-2-methyl-4-(2-dimethylaminoethylamino)pyrrolo[4,3-e]benzazepine.

EXAMPLE 15

Tablets of the following composition are compressed in a tableting press in a conventional manner.
  40 mg of substance of Example 1 (E)
  120 mg of corn starch
  13.5 mg of gelatin
  45 mg of lactose
  2.25 mg of Aeros ® (chemically pure silica in submicroscopically fine distribution)
  6.75 mg of potato starch (as 6% paste)

EXAMPLE 16

Sugar-coated tablets of the following composition are prepared in a conventional manner:
  20 mg of substance of Example 1 (E)
  60 mg of core composition
  60 mg of sugar-coating composition The core composition consists of 9 parts of corn starch, 3 parts of lactose and 1 part of Luviskol ® VA 64 (60:40 copolymer of vinylpyrrolidone and vinyl acetate, cf. Pharm. Ind. 1962, 586). The sugar-coating composition consists of 5 parts of sucrose, 2 parts of corn starch, 2 parts of calcium carbonate and 1 part of talc. The sugar-coated tablets prepared in this way are then provided with an enteric coating.

EXAMPLE 17

10 g of substance of Example 1 (E) are dissolved in 5000 ml of water with the addition of NaCl, and the pH is adjusted to 6.0 with 0.1N NaOH so that a solution which is isotonic with blood is produced. This solution is dispensed in 5 ml portions in ampules and sterilized.

We claim:
1. A 4-substituted 10-cyanomethylenepyrrolo[4,3-e]benzazepines of the formula I

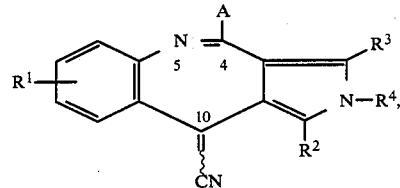

where $R^1$ is hydrogen or halogen, alkyl of 1 to 3 carbon atoms, trifluoromethyl or alkoxy of 1 to 3 carbon atoms, $R^2$ and $R^3$ are hydrogens or halogens, $R^4$ is hydrogen or alkyl of 1 to 3 carbon atoms or aralkyl where alkyl is of 1 to 3 carbon atoms and where the aromatic system may be substituted by halogen, $C_{1-3}$-alkyl or methoxy radical and A is an amino, $-NR^5R^6$ where $R^5$ and $R^6$ form, together with the nitrogen atom connecting them, a 5- to 7-membered saturated ring which may contain a nitrogen or oxygen as further hetero atom, it being possible for an additional nitrogen to be substituted by alkyl of 1 to 3 carbon atoms, hydroxyalkyl of 2 or 3 carbon atoms, alkoxyalkyl where alkyl or alkoxy is of 2 or 3 carbon atoms, cycloalkyl or cycloalkylmethyl with 3 to 7 carbon atoms in the cycloalkyl ring, alkynyl of 2 to 5 carbon atoms and additionally by oxygen in the form of a N-oxide, or A is an amino radical $-NHR^7$ where $R^7$ is aminoalkyl of 2 to 7 carbon atoms, it being possible for the amine nitrogen to be substituted by alkyl of 1 to 5 carbon atoms or to be a constituent of a 5- to 7-membered saturated ring which may contain a nitrogen or oxygen as further hetero atom, it being possible for a nitrogen which is present to be substituted by alkyl of 1 to 3 carbon atoms or hydroxyalkyl of 2 or 3 carbon atoms, and the physiologically tolerated acid addition salts thereof.

2. A compound of the formula I as claimed in claim 1, where $R^1$ is hydrogen, chlorine or fluorine and A is piperidinyl, piperazinyl or homopiperazinyl which are substituted on the ring nitrogen which is present where appropriate by hydrogen, methyl, ethyl, β-hydroxyethyl, cyclopropyl or propynyl and/or may be in the form of the N-oxide.

3. (E),(Z)-00-Cyanomethylene-4-(4-methyl-1-piperazinyl)pyrrolo[4,3-e]benzazepine.

4. (E)-10-Cyanomethylene-4-(4-methyl-1-piperazinyl)pyrrolo[4,3-e]benzazepine.

5. (Z)-10-Cyanomethylene-4-(4-methyl-1-piperazinyl)pyrrolo[4,3-e]benzazepine.

6. (E),(Z)-7-Chloro-10-cyanomethylene-4-(4-methyl-1-piperazinyl)pyrrolo[4,3-e]benzazepine.

7. A therapeutic composition for imparting to a patient a sedative, hypnotic, tranquilizer, muscle relaxant, neuroleptic or anti-parkinson effect, which comprises an effective amount of a compound as claimed in claim 1, and a pharmaceutically acceptable excipient.

8. The therapeutic composition as claimed in claim 7, which is in a form suitable for oral or parenteral administeration.

9. A method for imparting to a patient a sedative, hypnotic tranquilizer, muscle relaxant, neuroleptic or anti-parkinson effect, which comprises administering to said patient an effective amount of a compound as claimed in claim 1.

10. The method as claimed in claim 9, wherein a daily dose of said compound is from about 1 to 20 mg/kg of body weight for oral administration.

11. The method as claimed in claim 9, wherein a daily dose of said compound is from about 0.1 to 2 mg/kg of body weight for parenteral administration.

* * * * *